United States Patent [19]

Moore et al.

[11] Patent Number: 4,718,077

[45] Date of Patent: Jan. 5, 1988

[54] RADIOLUCENT TABLE FOR MEDICAL RADIOGRAPHY

[76] Inventors: Robert R. Moore, 4010 East Ave., Hayward, Calif. 94545; Steve R. Lamb, 2272 Sydney Way, Castro Valley, Calif. 94546

[21] Appl. No.: 711,671

[22] Filed: Mar. 14, 1985

[51] Int. Cl.⁴ ............................................... A61B 6/04
[52] U.S. Cl. ................................. 378/209; 269/71; 269/322
[58] Field of Search ............ 378/208, 209, 177; 269/322, 71, 73, 204; 108/137, 143

[56] References Cited

U.S. PATENT DOCUMENTS

| | | | |
|---|---|---|---|
| 2,152,058 | 3/1939 | King | 269/204 |
| 3,158,742 | 11/1964 | Morel et al. | 378/209 |
| 3,463,921 | 8/1969 | Warden | 378/209 X |
| 4,225,125 | 9/1980 | Lee | 269/322 |
| 4,452,439 | 6/1984 | Hogan | 378/209 X |
| 4,552,347 | 11/1985 | Wallis | 269/322 |
| 4,584,989 | 4/1986 | Stith | 378/209 X |

FOREIGN PATENT DOCUMENTS 1159891 7/1958 France ........................ 378/209

*Primary Examiner*—Frederick R. Schmidt
*Assistant Examiner*—Steven P. Schad
*Attorney, Agent, or Firm*—Bielen and Peterson

[57] ABSTRACT

An adjustable, radiolucent table for radioscopic examination of a medical patient lying thereon, the table including a radiolucent top, floor support structure connected at each end to the top of the support structure having apparatus permitting bidirectional movement of the table top enabling accurate movement of a patient thereon with respect to a radioscopic source, particularly for use in discolosis procedures.

3 Claims, 6 Drawing Figures

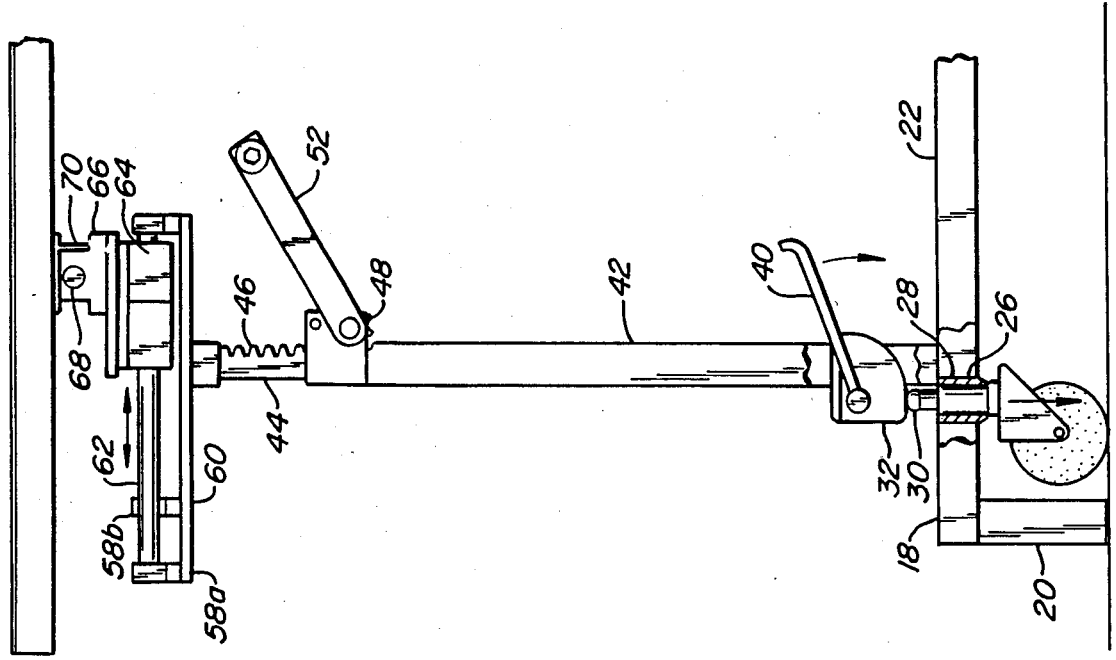
FIG._2.
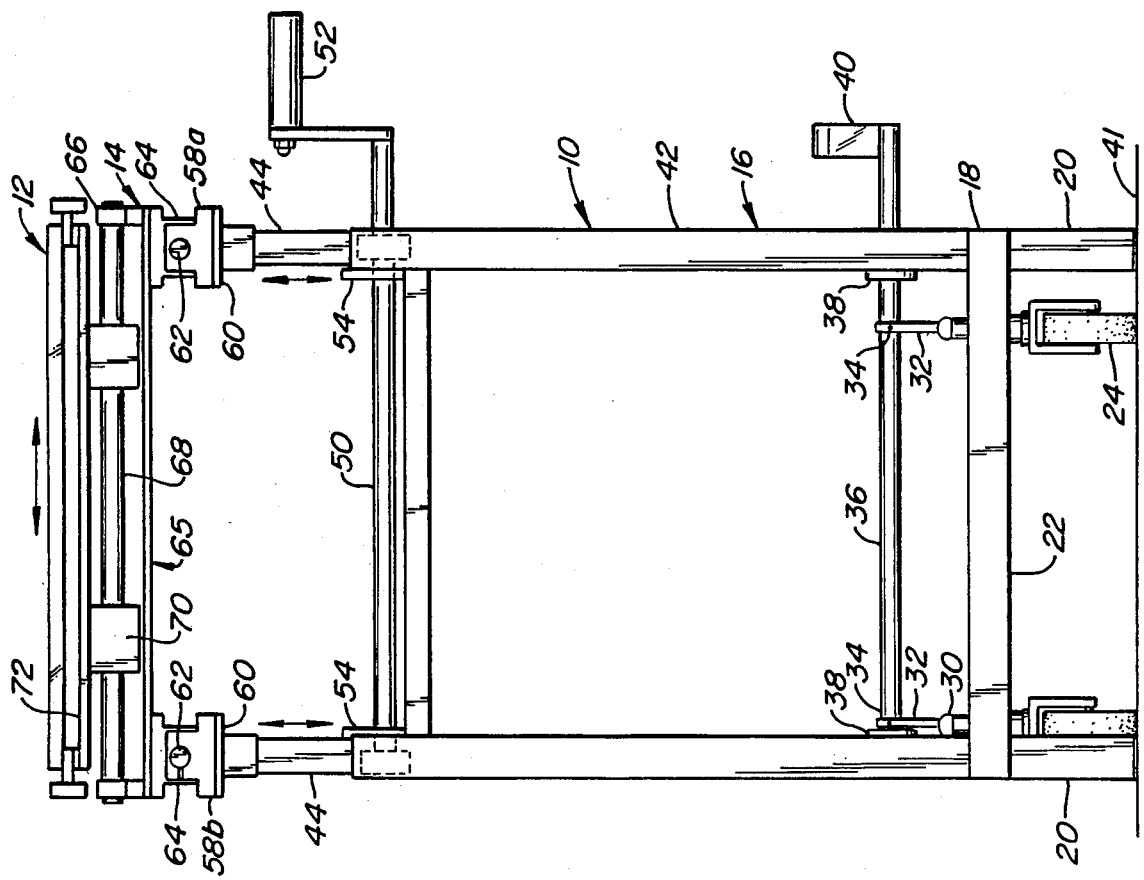
FIG._1.

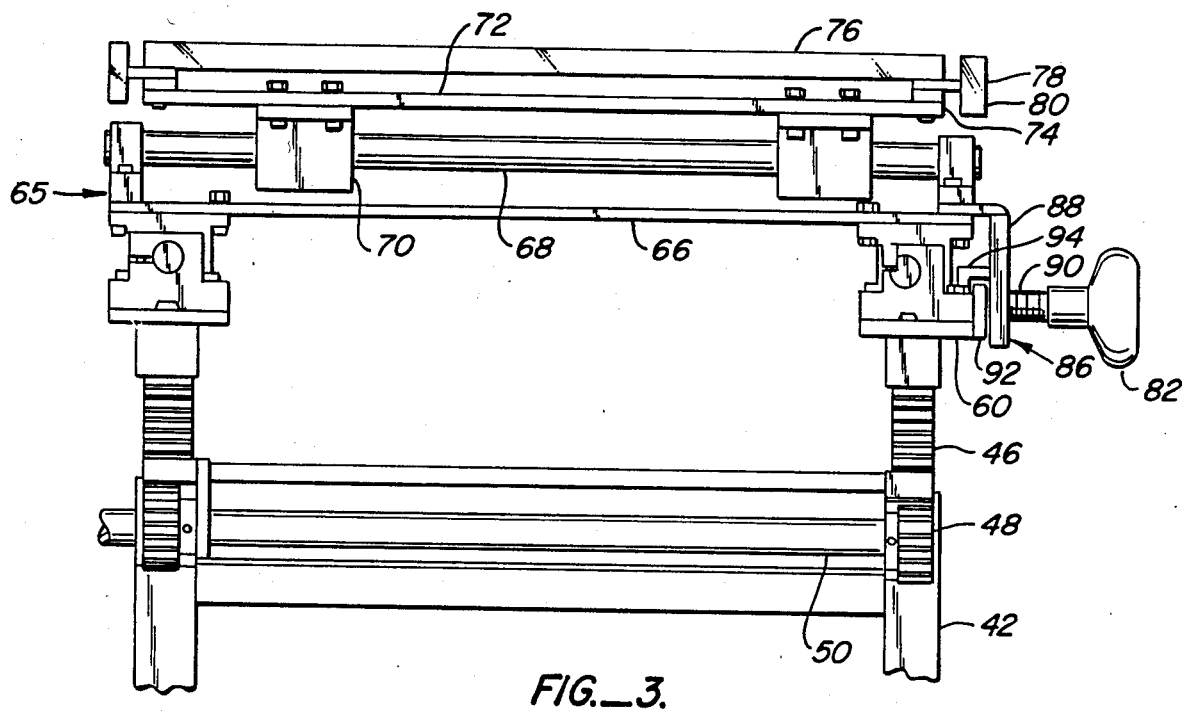
FIG._3.
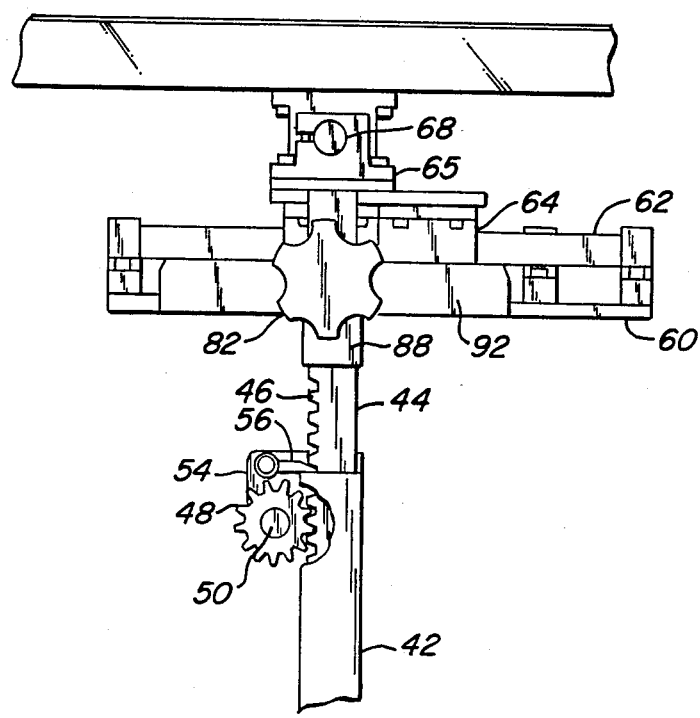
FIG._4.

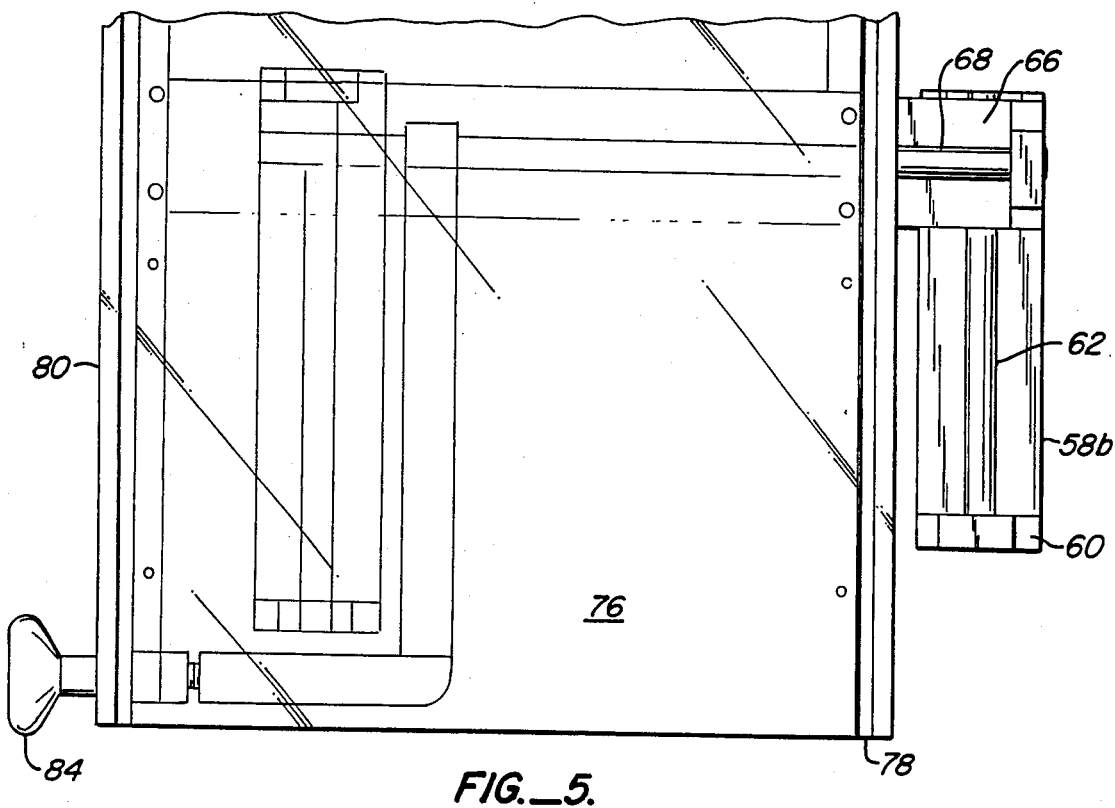
FIG._5.
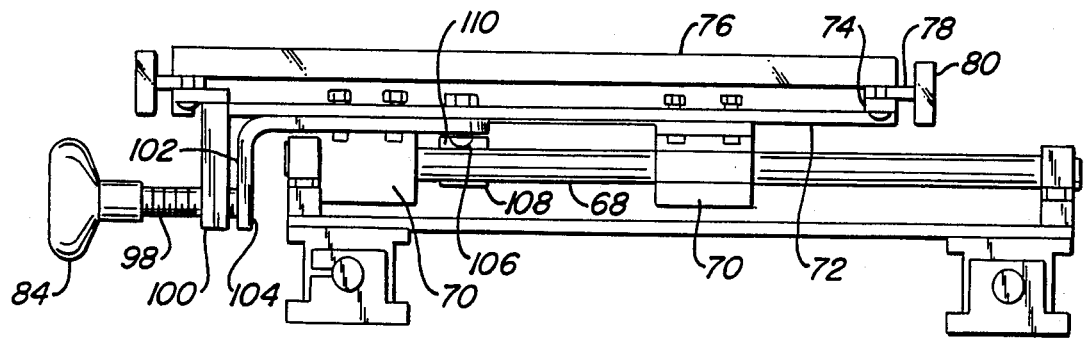
FIG._6.

RADIOLUCENT TABLE FOR MEDICAL RADIOGRAPHY

BACKGROUND OF THE INVENTION

This invention relates to medical apparatus, particularly apparatus for assisting radioscopic examinations where precision in the focus and targeting of radiation is desired. The apparatus of this invention comprises a radiolucent table top having support means for limited bidirectional movement of the top with respect to the radioscopic source.

In certain radiology procedures, for example in discolosis treatment by lamenectomy and particularly chemonucleolysis, it is desirable to position the radioscopic source directly over the affected spinal disc. Because of the weight and inherent inertia of the radioscopic source, usually a C-arm fluoroscope, the final targeting of the radiation beam is difficult to accurately control. Movement of a radiology table may also be difficult to control.

Targeting of the radiation beam is important in discolysis procedures because the affected disc is examined on edge, with the patent lying on the table in a lateral decubital. In discolysis, radioscopic examination may occur in diagnosis prepatory to treatment, and during injection of a lysing agent for disolving the nucleus pulposus in a herniated disc in chemonucleolysis procedures, again for accurate needle placement.

In chemonucleolysis procedures, particularly utilizing a needle guide apparatus as described in the patent entitled Needle Guide Apparatus for Discolysis Procedures, issued on Jan. 27, 1987, U.S. Pat. No. 4,638,799, apparatus adjustment and final location of the injection needle is monitored radioscopically with reference to radio-opaque indicator means. In order to accurately monitor the relative position of the apparatus with respect to the patient, the radiation beam should be centrally aligned with the indicator means. The fine adjustments necessary cannot be adequately obtained by movement of a conventional radiology table or radioscopic source.

Other radiological procedures for examination or treatment may require similar demanding adjustments not achievable by conventional apparatus.

In order to solve these problems, the radiolucent table extension of this invention was devised.

SUMMARY OF THE INVENTION

The radiolucent table of this invention is designed to accurately align a radioscopic target area on a prone patient with a radiation source such as a C-arm fluroscope. The table is relatively lightweight and mobile having casters with means to retract the casters to plant the table in a desired stationary position relative to the radioscope. The table has a radiolucent table top, that is conveniently adjusted in height and dual carriage means for longitudinal and transverse adjustment of the table top. The carriage means has a system of bearings for substantially friction free bidirectional movement in a horizontal plane, and locking means to lock the table top in the select position. In this manner, the target area of a patient on the table can be located with a minimum of effort and fine adjustments easily executed since only the table top and not the entire table is moved during alignment procedures. These and other advantages will become apparent from a detailed description of the preferred embodiment.

BRIEF DESCRIPTION OF THE DRAWINGS

FIG. 1 is an end elevational view of the radiolucent table.

FIG. 2 is a side elevational view partially fragmented illustrating one end of the table of FIG. 1.

FIG. 3 is a enlarged view, partially fragmented of the insider top portion of the table end taken on the lines 3—3 in FIG. 2.

FIG. 4 is an enlarge partially fragmented viewe of a portion of the table taken on the lines 3—3.

FIG. 5 is a top view, partially fragmented of the table of FIG. 1 with the top laterally displaced.

FIG. 6 is an end view of the table top of FIG. 5.

DETAILED DESCRIPTION OF THE PREFERRED EMBODIMENT

Referrring to FIGS. 1 and 2, the radiolucent table designated in general by the reference numeral 10 is shown having a radiolucent table top 12 mounted by means of a dual carriage system 14, to freely float with respect to a support structure with a bidirectional movement in a horizontal plane 3.

The support structure 16 comprises a base 18 having four support legs 20 dependent from a perimeter frame 22. Four complimentary casters 24 are mounted in sockets 26 in a cross brace 28 to provide a roller means for the table. The casters 24 ahve a protruding top segment 30 contacting a cam 32 fixed by a set screw 34 to a cross shaft 36 pivotally mounted in bearing brackets 38. the cross shaft is joined to a projecting foot crank 40 which on depressing in the direction illustrated in FIG. 2, extends the casters to contact the floor surface 41 and elevate the table for movement. A lift of the foot crank 40 retracts the casters and plants the support structure on the floor surface 41.

Upwardly extending from the perimeter frame 22 of the base 18 are four tubular supports 42 with telescoping extensions 44 having rack teeth 46 which engage pinion gears 48 as shown in FIGS. 3 and 4. The pinion gears 48 are mounted on cross shafts 50 (one shown) each having a hand crank 52 for raising and lowering the table top 12. The two cross shafts 50 are mounted in bearing brackets 54 fixed to the tubular supports 42 with one of the brackets on each shaft having a locking detent 56 to fix the elevation of the table top when engaged in the pinion gear 48 as shown in FIG. 4.

The free floating table top 12 is coupled to the underlying support structure 16 by the dual carriage system 14 providing bidirectional movement in a horizontal plane with respect to the support structure 16.

As shown in FIGS. 1 and 2, four first rail structures 58a and b have first support bracket members 60 which cap the top of the support extensions 44. In the vertical ends of the bracket members are clamped guide rods 62 positioned longitudinally to the length of the table. Slidably engaging the guide rods are a first set of bearing blocks 64, two of which are coupled to the fore rail structures 58a for added stability. The fore rail structures 58a are slightly longer than the aft rail structures 58b to accommodate the dual block arrangement, as shown in FIG. 2. The first slide bearing blocks 64 are attached to two second transverse rail structures 65 and include second supporting bracket members 66 which span the table interconnecting the opposed underlying bearing blocks 64. The bracket members 66 have guide rods 68 to which a second set of bearing blocks 70 are slidable engaged. The second set of bearing blocks 70 are connected to the underside of the table top 12 on cross braces 72 as shown in FIGS. 3 and 6. The cross braces 72 are fastened to an underlying perimeter frame 74 secured to the horizontally positioned radiolucent table panel 76 of the table top 12. A standard clamping rail 78 is secured between the peimeter frame 74 and table panel 76 to project the clamping surface 80 from the side of the table top.

As a result of this dual carriage construction the table top is freely slidable longitudinally along the length of the table support structure 16 by action of the first set of bearing blocks 64 on the first rail structures 58a and b, and, transversely across the table support structure 16 by action of the second set of bearing blocks 70 on the second rail structures 66.

Because the table top and moving segments of the dual carriage are low in mass, and since low friction bearing blocks are utilized to virtually eliminate drag, the table top is freely moveable bidirectionally in a horizontal plane even with the added weight of a patient lying prone for radioscopic treatment or examination.

In order to lock the table top in a desired position, two conveniently located hand knobs 82 and 84 lock the table top, respectively in the longitudinal and transverse directions. The locking mechanism 86 for the longitudinal direction includes in addition to the hand knob 82, a threaded support plate 88 mounted to one of the movable bracket members 66 of the second transverse rail structures 65. A threaded shaft 90 attached to the hand knob 82 is threaded through the support plate 88 to engage a stationary contact plate 92 mounted to one of the support bracket members 60 capping the top of the support extensions 44 as shown in FIGS. 3 and 4. By tightening the hand knob 82 forcing the end of the threaded shaft 90 against the contact plate 92, the table is locked in the longitudinal direction. A tab 94 fixed to the movable support plate 88 contacts the back of the contact plate 92 in the event the hand knob is overtightened to inhibit deformation of the support plate 88.

Transverse or lateral motion of the table is prevented upon engagement of a lateral locking assembly 96 shown in FIGS. 5 and 6. The locking assembly 96 includes a hand knob 84 similar to that of the locking mechanism 86 for the longitudinal direction. The hand knob 84 is attached to a threaded shaft 98 which is threaded through a support plate 100 to engage a contact face 102 of a brake arm 104. The L-shaped brake arm 104 is pivotally connected to a cross brace 72 by a pivot screw 106 such that an end portion 108 of the arm hooks around the guide rod 68 and cradles a friction pad 110 proximate the guide rod. On tightening the hand knob 84 and pivotally displacing the brake arm 104, the friction pad 110 is urged against the guide rod 68 to fix the lateral position of the table with respect to the support.

Since the table immobilizing foot crank 40, the table top elevating hand crank 52 and the two hand knobs 82 and 84 are all located on the fore side of the table, they are conveniently accessable to an operator adjusting the location of the table and table top under a device such as a C-arm fluoroscope where access to the aft side of the table is limited. Since the structural elements of the dual carriage and support structure are located at the ends and perimeter of the table, there is a substantial central area of the table top that is free and clear of obstructions for radioscopic targeting through the radiolucent panel.

While in the foregoing embodiments of the present invention have been set forth in considerable detail for the purpose of making a complete disclosure of the invention, it may be apparent to those of skill in the art that numerous changes may be made in such detail without departing from the spirit and principles of the invention.

What is claimed is:

1. A radiolucent table for radiography comprising:
   an elongated table top having a horizontally positioned radiolucent panel adapted to support a patient thereon for radiographic treatment or examination;
   a support structure constructed to support said table top, said support structure having a base with means for supporting said table top in an elevated position above a floor surface, and elevating means for raising and lowering said table top;
   a dual carriage mechanism interconnecting said table top and said support structure, said dual carriage mechanism having means for movement in two perpendicular directions for bidirectional movement of said table top in a horizontal plane relative to said support structure wherein said dual carriage mechanism comprises a first set of guide elements mounted on said support structure and a first set of slide elements slidably engaging said guide elements for coordinated movement of said slide elements in a first direction, and, a second set of slide elements and a second set of guide elements oriented transverse to said first set of guide elements and mounted to said first set of slide elements for coordinated movement of said slide elements in a second direction transverse to said first direction wherein said second set of slide elements are mounted to said table top; and
   locking means for locking said table top in a selected position relative to said support structure wherein said locking means includes a pair of manually operated hand knobs arranged along a common side of the table top, each knob selectively controlling the locking of the table top in one of the two directions of bidirectional movement, the arrangement positioning the knobs for convenient access to an operator adjusting and fixing the location of the table top on the support structure, wherein said locking means includes a stationary contact member mounted on said support structure and a moveable contact member mounted on at least one of said slide elements and means connected to one of said hand knobs for selectively engaging said stationary and moveable contact members to inhibit movement in the first direction, and wherein said locking means includes a table top connected contact device having a friction pad engageable with at least one of said guide elements, and means for urging said friction pad into engagement with said guide element to inhibit movement in said second direction.

2. The table of claim 1 wherein said means for selectively engaging said stationary and moveable contact members to inhibit movement in the first direction comprises a threaded shaft with an end face on said hand knob adapted to retractably urge said end face of the shaft into engagement with said stationary contact member.

3. The table of claim 1 wherein said means for urging said friction pad into engagement with said guide element comprises a threaded shaft on said hand knob with a contact member, and a pivot arm pivotally connected to said table top, said arm having a short extension end on which said friction pad is mounted, and a long extension end having a contact face engageable with the contact member of said threaded shaft, wherein select rotation of said threaded shaft into engagement with the contact face of said pivot arm, and, said friction pad into engagement with said guide element.

* * * * *